(12) United States Patent
Franckowiak

(10) Patent No.: US 8,464,710 B1  
(45) Date of Patent: Jun. 18, 2013

(54) DEVICE FOR AIDING INTUBATION

(76) Inventor: Melissa Franckowiak, Grand Island, NY (US)

(*) Notice: Subject to any disclaimer, the term of this patent is extended or adjusted under 35 U.S.C. 154(b) by 0 days.

(21) Appl. No.: 13/560,307

(22) Filed: Jul. 27, 2012

(51) Int. Cl.
- A61M 11/00 (2006.01)
- A61M 16/00 (2006.01)
- A61B 18/08 (2006.01)
- A61F 5/56 (2006.01)
- A61C 5/14 (2006.01)

(52) U.S. Cl.
USPC ........... 128/200.26; 128/200.15; 128/201.26; 128/206.29; 128/207.14; 128/848; 128/859; 128/860; 128/861

(58) Field of Classification Search
USPC ............. 128/200.15, 200.26, 207.14, 201.26, 128/206.29, 848, 859–861
See application file for complete search history.

(56) References Cited

U.S. PATENT DOCUMENTS

| | | | |
|---|---|---|---|
| 5,590,643 A | 1/1997 | Flam | |
| 5,655,528 A * | 8/1997 | Pagan | 128/207.14 |
| 5,746,202 A * | 5/1998 | Pagan | 128/207.14 |
| 6,257,238 B1 | 7/2001 | Meah | |
| 6,983,744 B2 * | 1/2006 | Alfery | 128/200.26 |
| 2008/0230055 A1 * | 9/2008 | NaPier | 128/200.26 |
| 2009/0050161 A1 | 2/2009 | Burdumy | |
| 2009/0211574 A1 * | 8/2009 | Sniadach | 128/200.26 |
| 2010/0170506 A1 * | 7/2010 | Pawels et al. | 128/200.26 |

* cited by examiner

Primary Examiner — Patricia Bianco  
Assistant Examiner — Brandon L Jackson  
(74) Attorney, Agent, or Firm — Vincent G. LoTempio; Kloss, Stenger & LoTempio

(57) ABSTRACT

A device for aiding intubation of a patient comprising a generally ovular palate bridge having a flexible convex surface to allow the device to conform to a roof of a patient's mouth and a flexible concave surface to allow for space in the mouth for placement of an endotracheal tube or to clear an oral airway which is attached to a teeth guard to prevent dental trauma and an esophageal block to block aspiration from a patient's stomach into a patient's lungs and to prevent erroneous intubation.

7 Claims, 6 Drawing Sheets

DEVICE FOR AIDING INTUBATION

BACKGROUND OF THE INVENTION

1. Field of the Invention

This disclosure relates generally to medical devices and an airway management device, trough (teeth guard), flexible guide piece and esophageal block. More specifically, the present disclosure allows placement of an oral airway device to move a tongue out of the way of blocking the trachea during ventilation, while combining the functions of blocking the esophagus, preventing air from being diverted down the trachea during bag-mask ventilation, preventing aspiration from below, and protection the teeth during laryngoscopy.

2. Background

Several devices have been invented to facilitate the insertion of intubation devices while keeping the oral airway open and mandible in a protracted position. For example U.S. Pat. No. 6,257,238, issued to Meah, discloses a bite block for upper gastrointestinal endoscopy having a tubular body defining channel, a shield connected to the tubular body, and a tongue depressor connected to the tubular body. The bite block has a chamber open to the channel in the bite block. A viscous bio-compatible lubricant in said chamber can contact and coat the end of an endoscope or other instrument when the instrument is inserted through the bite block. However, the '238 patent does not use a thin flexible guide piece that accommodates the shape of the soft/hard palate and connects a teeth guard to a conical piece.

U.S. Pat. No. 5,590,643, issued to Flam, discloses a mandibular protracting oral intubating airway with a rigid main body with a mouthpiece. The mouthpiece has an annular front flange and a bite guard extending a short distance rearwardly. A flat, generally C-shaped tongue retractor portion extends rearwardly from the rear flange of the bite portion and curves downwardly. When properly positioned in the mouth of a patient, the upper and lower teeth are retained in the grooves of the resilient sleeve with mandible protracted maximally forward relative to the maxilla. However, the '643 patent does not teach, motivate or suggest a mouth guard bound to an esophageal bougie or block. Moreover, the '643 patent does not teach motivate or suggest to protect the patient's teeth when an endotracheal tube is inserted.

U.S. Patent Application No. 2009/0050161, submitted by Burdumy, discloses a combination bite block, tongue depressor/retractor and airway for establishing and maintaining an open airway while preventing emergence clenching and the resulting dental and soft tissue damage associated with emergence clenching in procedures where the patient is not in control of their own airway. The bite block component is a wedge shaped, compressible component that is inserted between the upper and lower molars on either side of the mouth. The tongue depressor component is comprised of a flat portion that is inserted into the side of the bite block. However, this application does not teach, motivate or suggest a mouth guard connected to an esophageal bougie or block. Moreover, this application does not teach, motivate or suggest to protect the patient's teeth when an endotracheal tube is inserted.

U.S. Patent Application No. 2010/0249513, submitted by Tydlaska, discloses a laryngoscope system comprised of a handle, an arm, a camera, a light, and a disposable sheath. The sheath being comprised of a canal capable of being threaded with a bougie. The display unit is comprised of a container, a stand and a screen. The IV pole attachment is comprised of an attachment receiver. However, this application does not teach, motivate or suggest a mouth guard connected to an esophageal block. Moreover, this application does not teach, motivate or suggest to protect the patient's teeth when an endotracheal tube is inserted.

SUMMARY OF THE INVENTION

It is accordingly a primary object of the present invention is to provide a device for aiding intubation and ventilation having a mouth guard bound to an esophageal block that can be used quickly and easily to guide a tube, protect against dental trauma and block aspiration and erroneous intubation, which is critical when a patient is not breathing.

Another primary object of the present invention is to provide a device for aiding intubation and ventilation that prevents aspiration and prevents ventilation of the esophagus by blocking the esophagus and directing ventilation down the trachea.

Another object of the invention is to provide a device for aiding intubation and ventilation that slides into the patient's mouth quickly and easily either blindly or with the use of a tongue blade to aid placement, such as after induction of general anesthesia or in an emergency situation in the field.

Yet another object of the invention is to provide a device for aiding intubation and ventilation having a trough (teeth guard) to prevent dental trauma from the inappropriate placement of the laryngoscope blade of an endotracheal tube.

A further object of the invention is to provide a device for aiding intubation and ventilation for patients with prominent incisors or patients with anticipated difficult airway or difficult mask ventilation.

Another further object of the invention is to provide a device for aiding intubation and ventilation that blocks the esophagus from both ventilation and intubation while preventing reflux from below by consuming airspace in the esophagus.

The objects of the invention are achieved by provision of a device for aiding intubation and ventilation of a patient comprising a generally ovular palate bridge having a flexible convex surface to allow the device to conform to a roof of a patient's mouth and a flexible concave surface to allow for space in the mouth for placement of an endotracheal tube or to clear an oral airway, which is attached to a teeth guard to prevent dental trauma and an esophageal block to block aspiration from a patient's stomach into a patient's lungs and to prevent erroneous intubation.

Additional objects and advantages will become apparent and a more thorough and comprehensive understanding may be had from the following description and claims taken in conjunction with the accompanying drawings forming a part of this specification.

BRIEF DESCRIPTION OF THE DRAWINGS

The present invention and the manner in which it may be practiced is further illustrated with reference to the accompanying drawings wherein.

DETAILED DESCRIPTION OF THE INVENTION

Figure 1:
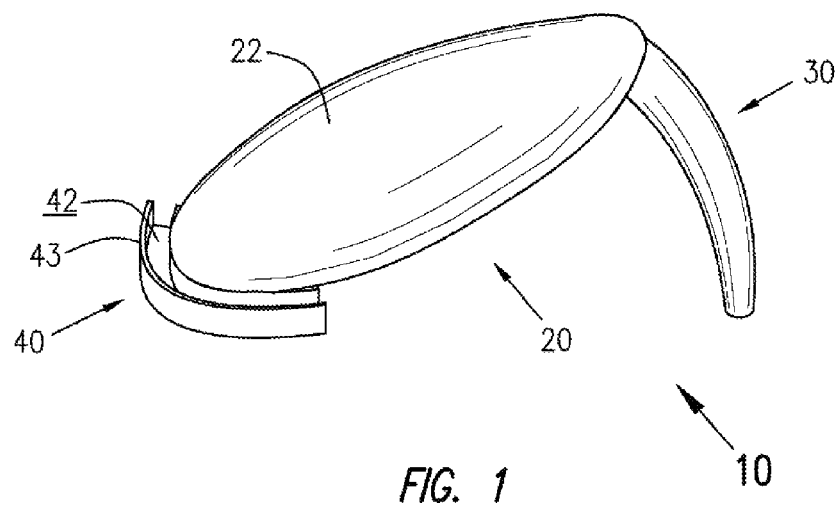
FIG. 1 is a front perspective view of a preferred embodiment of a device for aiding intubation of a patient showing the palate bridge, the esophageal conical block and the teeth guard.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. §112. Additionally, in standard anatomical language and drawings a sagittal plane is a vertical plane, which passes from ventral (front) to dorsal (back); dividing the body into right and left halves. This description refers to the diagrams showing the device for aiding intubation, and endotracheal tube in situ, which are sagittal sections as "cross sections."

Adverting now to the drawings, with reference to FIG. 1, a preferred embodiment of the present disclosure of a device for aiding intubation of a patient is indicated generally by numeral 10. This disclosure relates to medical airway management device for aiding intubation of a patient comprising a centrally positioned generally ovular palate bridge 20 having a first end and second end and a teeth guard to prevent dental trauma attached to the first end of the palate bridge and an esophageal block 30 attached to the second end of the ovular palate bridge to block aspiration from a patient's stomach into a patient's lungs and to prevent erroneous intubation. The esophageal block is preferably constructed from a non-toxic latex or rubber like material. Ventilation of air down the esophagus leads to abdominal distention which can further encourage aspiration of acidic gastric contents up the esophagus and into the trachea, which can result in a lethal aspiration pneumonia.

The preferred embodiment of the present disclosure of a device for aiding intubation of a patient allows placement of an oral airway device to move a tongue out of the way of blocking the trachea during ventilation, while combining the functions of blocking the esophagus, preventing air from being diverted down the trachea during bag-mask ventilation, preventing aspiration from below, and protection the teeth during laryngoscopy. The present disclosure combines these functions in one device, which is important due to the limited space for such devices in the oral cavity and oropharynx. The present disclosure facilitates the insertion of such devices as an endotracheal tube. In blocking the esophagus during laryngoscopy, the invention not only acts as a guide in placement of the endotracheal tube in the proper orifice, the trachea, by preventing its placement in the incorrect orifice, the esophagus, but also is intended to prevent aspiration of gastric contents from below. The application of manual cricoid pressure externally and applied on the neck to occlude the esophagus during laryngoscopy in cases deemed to be at risk for aspiration of gastric contents has been practiced, but has not definitively been proven to be effective to prevent aspiration.

FIG. 1 is a front perspective view the present disclosure of a device for aiding intubation of a patient showing palate bridge 20, a conical esophageal block 30 and teeth guard 40. The elements of the present disclosure each serve unique functions that when bound together are more functional than either alone due to the limited time available during the usage of the present disclosure namely, during intubation of the trachea. While other teeth or mouth guards exist, none is bound to an esophageal bougie or block. A common problem during intubation is unintended damage to the patient's teeth, especially when the procedure is performed by inexperienced operators, or the patient has tooth decay or brittle teeth. The device for aiding intubation of a patient having both an esophageal block and mouth guard is placed in the patient's mouth and esophagus after the induction of general anesthesia. The device for aiding intubation of an anesthetized patient acts as an esophageal block, which prevents the endotracheal tube from entering the patient's esophagus, while protecting the teeth during intubation with teeth guard 40.

FIG. 1 illustrates a generally C-shaped, teeth guard, manufactured from a thick piece plastic like material that is sturdy enough to protect the teeth against damage from the inappropriate placement of a laryngoscope blade or other medical instrument. It should be appreciated that the teeth guard can be constructed from other suitable materials that would protect the patient's teeth while being safe for surgical use, such as rigid rubber or plastic like material. FIG. 1 illustrates teeth guard 40 with slot 42 into which the patient's teeth insert. The teeth are the upper incisors and lateral canines. In the preferred embodiment of the present disclosure, the teeth are covered anteriorly, posteriorly and inferiorly by cephalic opening 43, holding the device in place and protecting the teeth from damage during intubation. Protecting the patient's teeth from dental trauma is important because dental damage is a common complication during laryngoscopy in patients with tooth decay, brittle teeth and patients being treated by inexperienced laryngoscopists. Although the teeth guard protects the patient's teeth, caution must still be exercised and laryngoscopy must be performed with proper technique. Device for aiding intubation of a patient 10 slides into the patient's mouth quickly and easily either blindly or with the use of a tongue blade to aid placement, such as after induction of general anesthesia or in an emergency situation in the field.

In addition, the teeth guard must not be so thick as to impede laryngoscopic visualization or to prevent the placement of laryngoscope blade.

The teeth guard is secured to a flexible palate bridge 20. The palate bridge is ovular allowing it to easily slide into the roof of a patient's mouth. It should be appreciated that the palate bridge can be any generally oval or circular shape having a flexible convex surface 22 which fits inside the mouth of the patient and flexibly conforms in the general shape of the roof of the patient's mouth and a flexible concave surface to allow for space in the mouth for placement of an endotracheal tube or to clear an oral airway. Teeth guard 40 is attached to a first end of palate bridge 20 and esophageal conical block 30 is attached to a second end of palate bridge 20. The palate bridge is preferably formed of polyvinylchloride (PVC), polypropylene or some other flexible material.

The esophageal block has a tubular tapered shape, narrowing from a nexus connection point at the second end of the palate bridge to a distal end of the esophageal block. During intubation the esophageal block is the first part of device for aiding intubation of a patient 10 to enter the patient's mouth; serving as a means to block the esophagus from both ventilation and intubation. The esophageal block prevents reflux from below by consuming space in the esophagus by which reflux may occur and by blocking ventilation through the esophagus to the stomach, also by consuming space and thereby directing an endotracheal tube for ventilation down the intended route, through the trachea, so it can ventilate the lungs. To prevent erroneous placement of endotracheal tube into the esophagus, the esophageal block consumes the empty space by which endotracheal tube passage may erroneously occur. A typical esophageal block is approximately in the range of 25 to 45 mm in diameter to consume the space necessary to fully block the esophagus.

Figure 2:
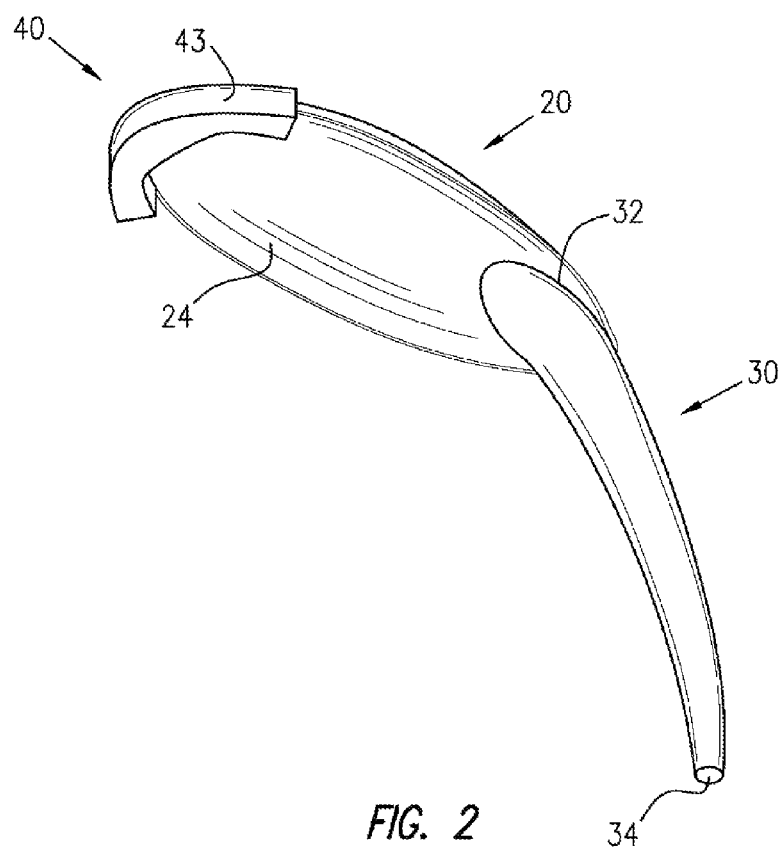
FIG. 2 is a bottom perspective view of the present disclosure showing the concave surface of the palate bridge.

FIG. 2 is a bottom perspective view of a device for aiding intubation of a patient showing concave surface 24 of the palate bridge. Teeth guard 40 is shown with cephalic opening 43. The teeth guard provides a cushion should the anesthetized patient attempt to bite down while falling out of consciousness. FIG. 2 illustrates a flexible concave surface 24 of palate bridge 20. It should be appreciated the concave surface of palate bridge is flexibly constructed to change shape and can be concave or flat. In either case, the concave surface of palate bridge is flexibly constructed to conform to the roof of a patient's mouth. FIG. 2 illustrates the underside of conical esophageal block 30, which connects to the palate bridge at the nexus connection point 32. It should be appreciated that the palate bridge and esophageal block can be one continuous device without a nexus connection point. Esophageal block 30 has a conical shape so as to slide smoothly down patient's esophagus. Additionally, the conical shape acts as a guide allowing the endotracheal tube to slide down into patient's trachea. Distal end 34 of esophageal block 30 is cylindrical in shape creating an obstructing surface used to prevent the endotracheal tube from entering patient's esophagus.

Figure 3:
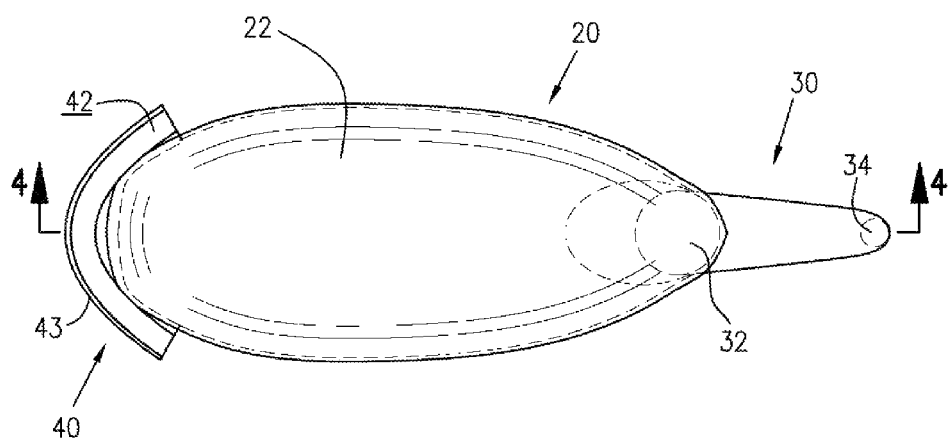
FIG. 3 is a top view of a preferred embodiment of a device for aiding intubation of a patient showing the convex surface of the palate bridge.

FIG. 3 is a top view of a device for aiding intubation of a patient showing the inner surface of the palate bridge. Teeth guard 40 with slot 42 is curved to conform to shape patient's teeth, specifically the upper incisors and the lateral canines. Teeth guard 40 has cephalic opening 43 to further protect the patient's teeth. Convex surface 22 of palate bridge 20 is convex as to replicate the curve of the roof of a mouth. At the end of the palate bridge opposite the teeth guard is nexus connection point 32, which connects the palate bridge to the esophageal block. The nexus connection point is circular allowing for a secure marriage between the palate bridge and esophageal block without compromising the functionality of the device for aiding intubation. of a patient It should be appreciated the nexus connection point can be constructed out of any plastic like material suitable for medical use such as non-toxic polyurethane or flexible PVC, and of any generally ovular shape that does not prevent the device for aiding intubation of a patient from functioning properly. FIG. 3 illustrates distal end 34 of esophageal block 30 at the opposite end of the nexus connection point. Distal end 34 of esophageal block 30 is the first part of the device for aiding intubation of a patient to enter patient's mouth.

Figure 4:
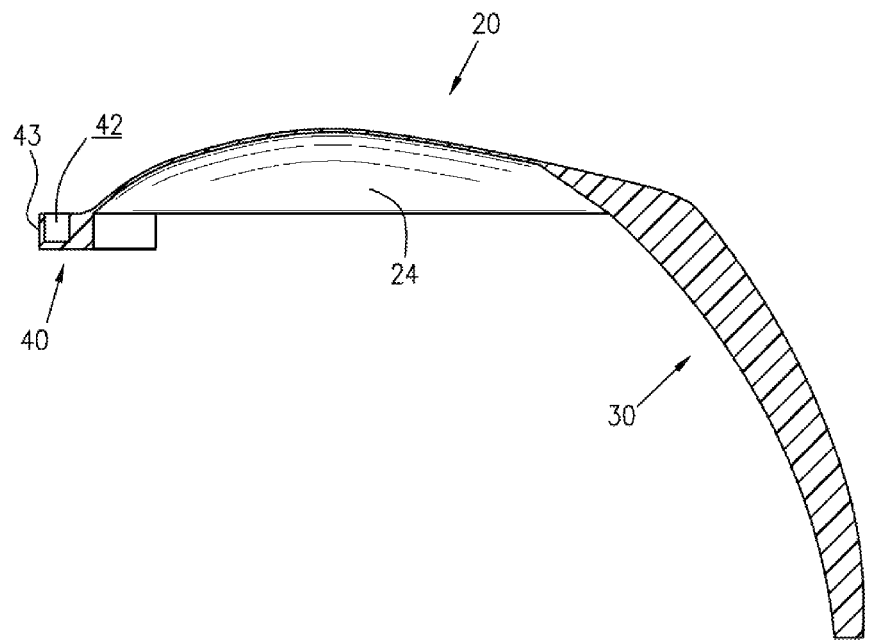
FIG. 4 is a side cross-sectional view of a preferred embodiment of a device for aiding intubation of a patient taken generally along line of FIG. 3.

FIG. 4 is a side cross-sectional view of a preferred embodiment of a device for aiding intubation of a patient taken generally along line of FIG. 3 illustrating the outer surface of the palate bridge. It should be appreciated that the concave surface 24 of palate bridge 20 is a flexible plastic or rubber like sheet that can conform to the roof of a mouth so as to allow an endotracheal tube to easily slide along the inner concave surface of the palate bridge. Teeth guard 40 is at the first end of the palate bridge. FIG. 4 illustrates slot 42 where patient's teeth, specifically the upper incisors and the lateral canines, insert. Teeth guard 40 has cephalic opening 43 to further protect the patient's teeth. FIG. 4 illustrates conical esophageal block 30 extending from the palate bridge. Esophageal block 30 is cylindrical at the nexus connection point, narrowing to conical at the distal end conforming to shape of esophagus and to aid gentle placement down esophagus to the patient's posterior pharynx and esophagus to guide an endotracheal tube into patient's trachea.

Figure 5:
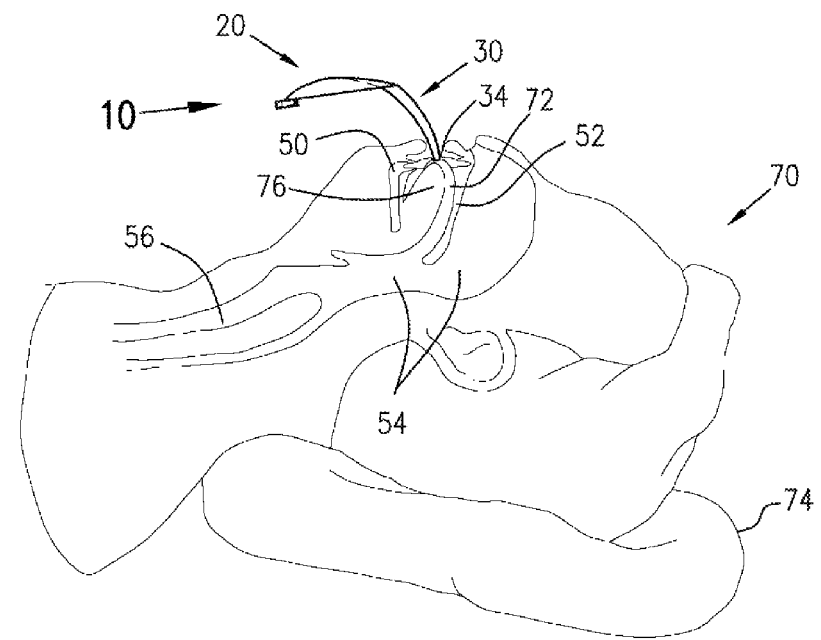
FIG. 5 illustrates a cross sectional view of a patient's upper anatomy and of a preferred embodiment of a device for aiding intubation of a patient positioned prior to insertion into patient's mouth.

FIG. 5 illustrates a cross section view patient's upper anatomy and a device for aiding intubation of a patient prior to inserting the device into a patient's mouth. Device for aiding intubation of a patient 10 is inserted into mouth 72 of patient 70 between mandible 50 and hard palate 52. The device for aiding intubation of a patient is inserted with distal end 34 of esophageal block 30 entering first and pressing tongue 76 downward to create an unobstructed path for the device for aiding intubation of a patient. The laryngoscopist can use palate bridge 20 as an insertion handle and means to guide the device for aiding intubation of a patient to the desired position. FIG. 5 illustrates the desired position for patient's head, lying elevated on pillow 74 so trachea 56 and posterior pharynx 54 are aligned to form a clear pathway for the endotracheal tube. It should be understood that the patient is under general anesthesia unconscious or apneic at the time of insertion, the device of the present disclosure is not intended for use in awake patients with an intact gag reflex.

Figure 6:
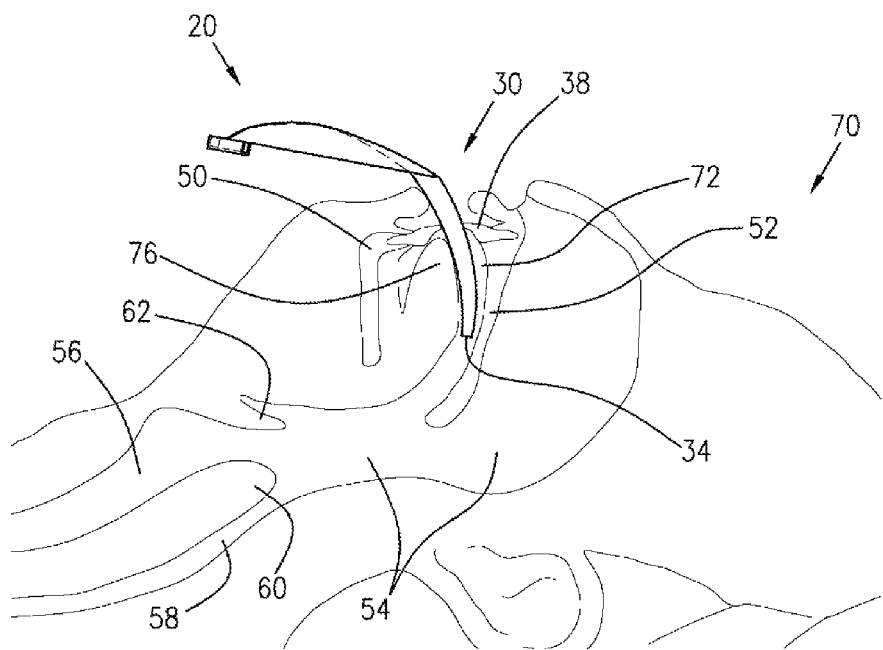
FIG. 6 is a cross sectional side view of a patient's upper anatomy and a preferred embodiment of a device for aiding intubation of a patient partially inserted into the patient's mouth.

FIG. 6 is a cross sectional side view of a patient's upper anatomy and a preferred embodiment of a device for aiding intubation of a patient partially inserted into the patient's mouth. Esophageal block 30 is partially inserted between mandible 50 and hard palate 52. The laryngoscopist must exercise caution when inserting the device for aiding intubation of a patient past teeth 38. Palate bridge 20 acts as an insertion handle allowing the device for aiding intubation of a patient to slide smoothly into mouth 72 of patient 70. FIG. 6 illustrates esophageal block 30 sliding over tongue 76. Distal end 34 of esophageal block 30 enters the mouth of patient first, and is ultimately maneuvered past posterior pharynx 54 to esophagus 58 just below soft tissue 60. This is the optimal position to ensure an endotracheal tube passes epiglottis 62 and enters the trachea 56 and not the esophagus.

Figure 7:
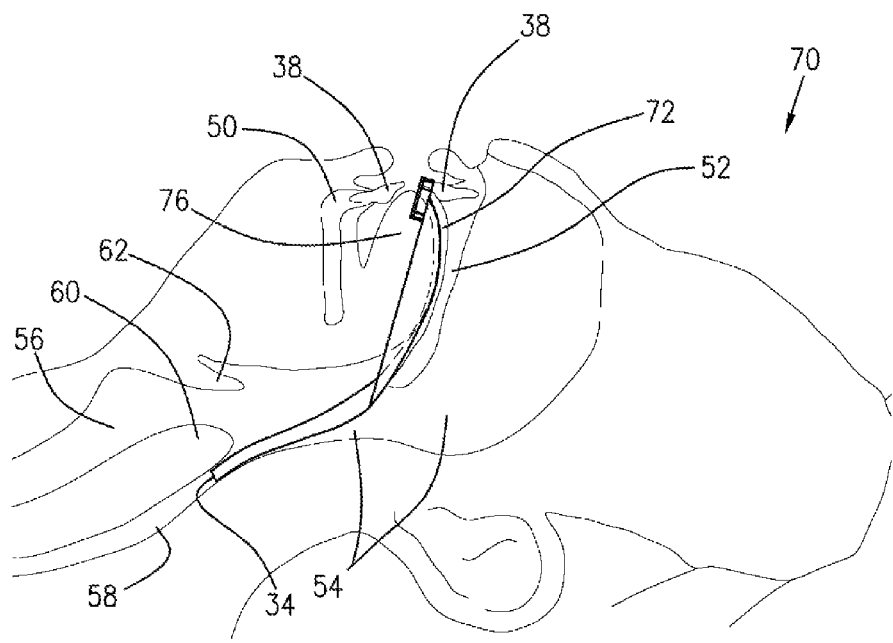
FIG. 7 is a cross sectional side view of patient's upper anatomy and a preferred embodiment of a device for aiding intubation of a patient fully inserted into patient's mouth.

FIG. 7 is a cross sectional side view of patient's upper anatomy and a preferred embodiment of a device for aiding intubation of a patient fully inserted into mouth 72 patient 70 with the teeth block in the preferred position for protecting teeth 38. FIG. 7 illustrates a device for aiding intubation of a patient securely positioned between mandible 50 and hard palate 52 with the esophageal block in the preferred position. The esophageal block consumes any empty space in the esophagus to prevent erroneous intubation. However, it should still be appreciated that caution and skill is still required from the professional performing the intubation. Distal end 34 of the esophageal block is positioned slightly past soft tissue 60 in esophagus 58 to prevent endotracheal tube from entering patient's esophagus. Although the figure is simplified to show the relevant parts of the upper anatomy of patient 70, it should be understood that soft tissue 60 is generally comprised of the soft tissues of posterior pharynx and laryngeal cartilages. FIG. 7 illustrates the convex surface of the palate bridge conforming to the roof of the patient's mouth with the entire palate bridge resting above tongue 76, naturally adhering to the hard palate on its undersurface with the patients saliva. The nexus connection point is positioned at posterior pharynx 54. It should be appreciated that the flexible nature of the palate bridge and the esophageal block allow the device for aiding intubation of a patient to conform to the curvature of the posterior pharynx while still providing space to allow an endotracheal tube move past epiglottis 62 and enter trachea 56.

Figure 8:
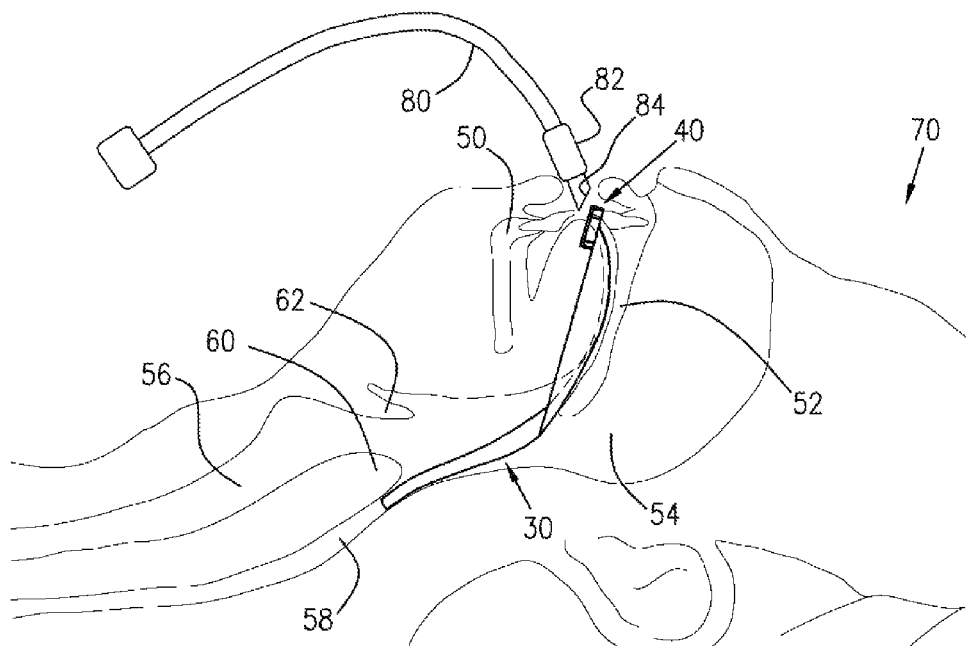
FIG. 8 is a cross sectional side view of a patient's upper anatomy and of a preferred embodiment of a device for aiding intubation of a patient fully inserted into patient's mouth with an endotracheal tube entering patient's mouth.

FIG. 8 is a cross sectional side view of a patient's upper anatomy and of a preferred embodiment of a device for aiding intubation of a patient fully inserted into patient's mouth with an endotracheal tube entering patient's mouth. As intubation begins, esophageal block 30 is the preferred position past posterior pharynx 54 with the distal end resting below soft tissue 60, consuming space in esophagus 58. FIG. 8 illustrates teeth guard 40 protecting the patient's teeth from cuff 82 and lumen 84 of endotracheal tube 80. Lumen 84 is an angular cut of the tube partially showing internal cavity of the endotracheal tube. A typical endotracheal tube has an internal cavity diameter of 7 mm. Again, caution and expertise is still required; however, the teeth guard provides an added means of protection to the upper incisors and lateral canines when the when the laryngoscope and endotracheal tube are inserted and passes through the mouth of patient 70. The palate bridge creates ample space between mandible 50 and hard palate 52 allowing the endotracheal tube a clear path past epiglottis 62 into trachea 56.

Figure 9:
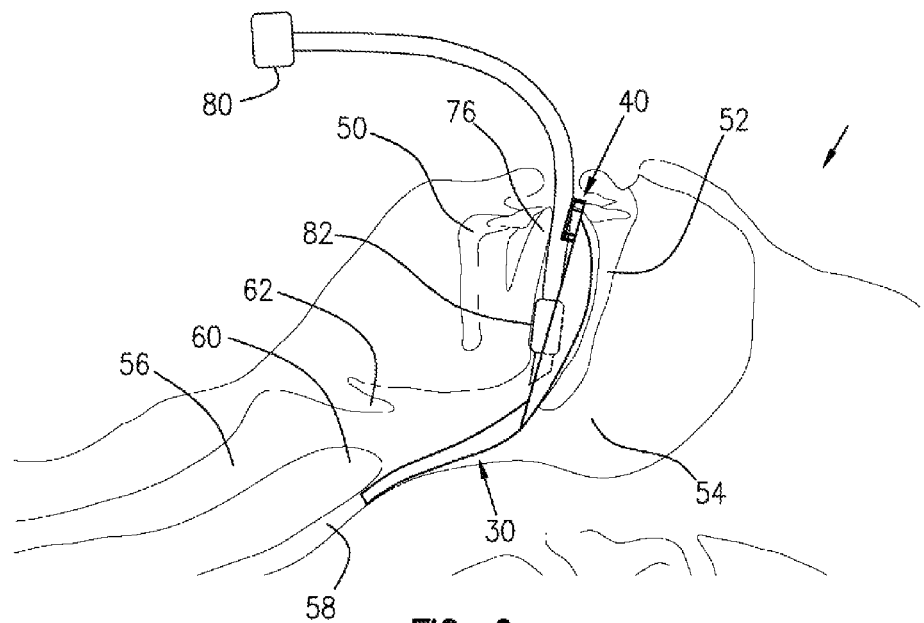
FIG. 9 is a cross sectional side view of a patient's upper anatomy and of a preferred embodiment of a device for aiding intubation of a patient fully inserted into patient's mouth with an endotracheal tube entering patient's airway.

FIG. 9 is a cross sectional side view of a patient's upper anatomy and of a preferred embodiment of a device for aiding intubation of a patient fully inserted into patient's mouth with an endotracheal tube entering patient's airway. FIG. 9 illustrates endotracheal tube 80 partially inserted into patient's mouth with cuff 82 just past tongue 76. Endotracheal tube 80 is buffered around the patient's upper teeth by teeth guard 40. The palate bridge rests below hard palate 52 and forms a curved in path allowing the endotracheal tube enough space to pass through the mouth without positioning mandible 50 of patient 70 at awkward angle or opening. FIG. 9 illustrates the teeth guard, the concave surface and the convex surface of the palate bridge working in concert to protect patient's teeth and mouth while also assisting the intubation process by creating a pathway for endotracheal tube past epiglottis 62 to trachea 56. Additionally, esophageal block 30, when in place, rests above posterior pharynx 54, with the distal end just below soft tissue 60. The esophageal block provides additional visual guidance during direct laryngoscopy for endotracheal tube, while also protecting esophagus 58 from erroneous intubation.

Figure 10:
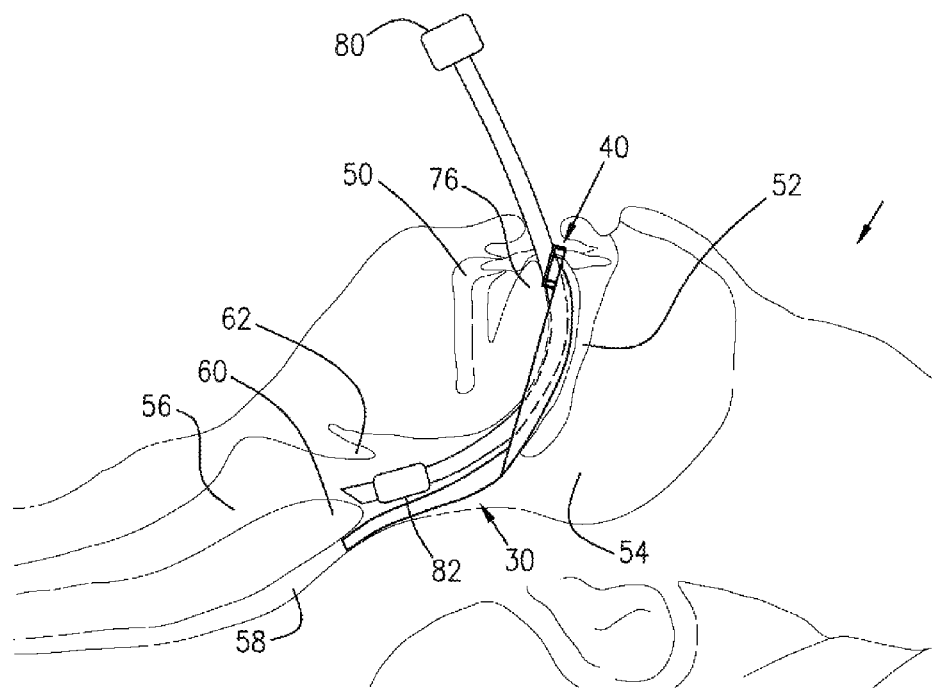
FIG. 10 is a cross sectional side view of a patient's upper anatomy and a preferred embodiment of a device for aiding intubation of a patient fully inserted into patient's mouth with the head of an endotracheal tube positioned between patient's soft tissues and epiglottis, and esophageal block in place preventing endotracheal tube from entering esophagus.

FIG. 10 is a cross sectional side view of a patient's upper anatomy and a preferred embodiment of a device for aiding intubation of a patient fully inserted into patient's mouth with the cuff of an endotracheal tube positioned between patient's soft tissues and epiglottis, and esophageal block in place preventing endotracheal tube from entering esophagus. FIG. 10 shows endotracheal tube 80 inserted into the patient's mouth, with teeth guard 40, the convex surface and concave surface of the palate bridge working in concert to protect patient's teeth and mouth while also assisting the intubation process by creating a pathway for endotracheal tube to trachea 56. Teeth guard 40 prevents dental trauma by protecting the patient's upper incisors and lateral canines from the endotracheal tube. The concave shape and convex shape of the surface of the palate bridge provide a further guide as the endotracheal tube passes above mandible 50 and tongue 76 and below hard palate 52, entering posterior pharynx 54 of patient 70. FIG. 10 shows cuff 82 of endotracheal tube 80 positioned between patient's soft tissue 60 and epiglottis 62. The soft tissues of posterior pharynx and laryngeal cartilages divide trachea 56 and esophagus 58. Without the esophageal block 30 of the device for aiding intubation of a patient, the endotracheal tube could easily pass into the patient's esophagus instead of the trachea, taking the most likely route when devices are inserted blindly into the pharynx. Operator skill and a laryngoscope or fiber optic light source are additionally generally required to guide placement of an endotracheal tube into its proper orifice, the trachea. However, with conical esophageal block 30 positioned at the posterior pharynx and occupying space in the patient's esophagus, the endotracheal tube is prevented from entering the esophagus and directed towards the trachea. The trachea must be visually identified during direct laryngoscopy and visualization of the correct structure is assisted by blocking the incorrect structure, the esophagus, with the esophageal block.

Figure 11:
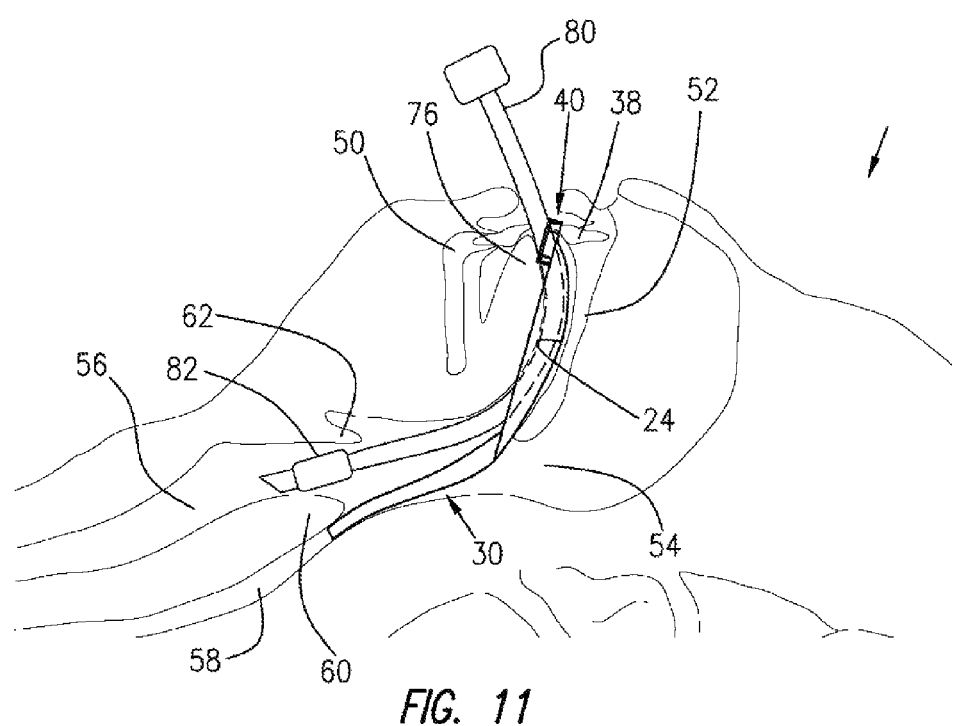
FIG. 11 is a cross sectional side view of a patient's upper anatomy and a preferred embodiment of a device for aiding intubation of a patient fully inserted into the patient's mouth with endotracheal tube at entrance of patient's trachea and esophageal block in place.

FIG. 11 is a cross sectional side view of a patient's upper anatomy and a preferred embodiment of a device for aiding intubation of a patient fully inserted into the patient's mouth with endotracheal tube at entrance of patient's trachea and esophageal block in place. FIG. 11 shows endotracheal tube 80 inserted into patient's mouth with the teeth guard, the convex surface and the concave surface of the palate bridge working in concert to protect patient's teeth and mouth, while also assisting the intubation process by creating a pathway for endotracheal tube to trachea 56, and keeping mandible 50 to open at an angle wide enough to provide ample space for laryngoscopist to perform the procedure. Concave surface 24 of the palate bridge emulates the roof of patient's mouth acting as a guide as the endotracheal tube passes through between tongue 76 and hard palate 52. FIG. 11 illustrates esophageal block 30 preventing the endotracheal tube from entering esophagus 58, while also guiding cuff 82 of endotracheal tube 80 between soft tissue 60 and epiglottis 62 into trachea 56. The distal end of the esophageal block rests in the esophagus. FIG. 11 illustrates all the individual elements of the device for aiding intubation of a patient working in concert to provide protection of teeth and esophagus, act as a guide for a medical device such as an endotracheal tube and act as a block, stopping the tube from entering the esophagus and preventing aspiration during the intubation process. Teeth block 40 protects teeth 38 of patient 70 from dental trauma by preventing injury from insertion of a laryngoscope and the endotracheal tube from contacting any of the patient's teeth. The nexus connection point is positioned just below posterior pharynx 54 further directing the endotracheal tube towards trachea 56. Esophageal block 30 extends from the nexus connection point and extends into esophagus 58. FIG. 11 illustrates the esophageal block working as desired, occupying space in the esophagus and directing the cuff 82 of endotracheal tube 80 from the esophagus and into the patient's trachea.

Although the invention as been described with reference to certain preferred embodiments, it will be appreciated by those skilled in the art that modifications and variations may be made without departing from the spirit and scope of the invention. It should be understood that applicant does not intend to be limited to the particular details described above and illustrated in the accompanying drawings. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A device for aiding intubation of a patient comprising: a generally ovular palate bridge having a first end and second end wherein said ovular palate bridge has a flexible convex surface to allow the device to conform to a roof of a patient's mouth and a flexible concave surface to allow for space in the mouth for placement of an endotracheal tube or to clear an airway; a teeth guard to prevent dental trauma attached to said first end of said ovular palate bridge; and an esophageal block attached to said second end of said ovular palate bridge to block aspiration from a patient's stomach into a patient's lungs and to prevent erroneous intubation wherein said esophageal block is shaped to model a patient's posterior pharynx and esophagus.

2. The device for aiding intubation of a patient of claim 1 wherein said teeth block is generally C-shaped to protect the upper incisors and lateral canines during intubation.

3. The device for aiding intubation of a patient of claim 2 wherein said teeth guard includes a slot for securing the device to the patient's teeth to prevent dental trauma during intubation.

4. The device for aiding intubation of a patient of claim 3 wherein said teeth guard includes a cephalic opening around teeth anteriorly and posteriorly to prevent dental trauma.

5. The device for aiding intubation of a patient of claim 1 wherein said esophageal block is conical, narrowing from a nexus connection point at said second end of said ovular palate bridge to a distal end of said esophageal block.

6. The device for aiding intubation of a patient of claim 5 wherein said esophageal block narrows to a conical flat end.

7. The device for aiding intubation of a patient of claim 1 wherein said ovular palate bridge has a generally circular shape.

* * * * *